US008415299B2

(12) United States Patent
Hooge et al.

(10) Patent No.: US 8,415,299 B2
(45) Date of Patent: Apr. 9, 2013

(54) METHODS FOR IMPROVED AVIAN PERFORMANCE

(76) Inventors: Danny Michael Hooge, Eagle Mountain, UT (US); Robert Frederick Wideman, Jr., Fayetteville, AR (US); Wayne John Kuenzel, Fayetteville, AR (US)

( * ) Notice: Subject to any disclaimer, the term of this patent is extended or adjusted under 35 U.S.C. 154(b) by 953 days.

(21) Appl. No.: 11/176,771

(22) Filed: Jul. 7, 2005

(65) Prior Publication Data

US 2006/0008510 A1     Jan. 12, 2006

Related U.S. Application Data

(60) Provisional application No. 60/586,104, filed on Jul. 7, 2004.

(51) Int. Cl.
*A61K 38/22* (2006.01)
*A61K 38/00* (2006.01)

(52) U.S. Cl. ............................................ 514/9.7; 514/9.8

(58) Field of Classification Search .................. 514/560, 514/4.8, 9.7, 9.8
See application file for complete search history.

(56) References Cited

U.S. PATENT DOCUMENTS

| | | | |
|---|---|---|---|
| 2,329,445 | A | 9/1943 | Turner et al. |
| 2,379,842 | A | 7/1945 | Turner et al. |
| 2,385,117 | A | 9/1945 | Turner et al. |

FOREIGN PATENT DOCUMENTS

| | | |
|---|---|---|
| GB | 492265 | 9/1938 |
| GB | 568183 | 3/1945 |
| GB | 598679 | 2/1948 |
| GB | 598680 | 2/1948 |

OTHER PUBLICATIONS

Boulakoud et al., "Thyroxine treatment induces changes in hypothalamic gonadotropin-releasing hormone characteristic of photorefractoriness in starlings (*Sturnus vulgaris*)", General and Comparative Endocrinology, vol. 82, No. 1, pp. 78-85 (1991), see enclosed abstract.*
Szelenyi et al., "Thyroxin Induced Moult in Domestic Hen", Acta Physiologica Hungarica, vol. 72, No. 2, pp. 143-149 (1988).*
Lien et al., "Effects of Thyroidectomy on Egg Production, Molt, and Plasma Thyroid Hormone Concentration of Turkey Hens", Poultry Science, vol. 68, No. 8, pp. 1126-1132 (Aug. 1989).*
R. Albuquerque et al., Effect of Different Methods of Forced Molt on Performance of Laying Hens. Braz. J. Vet. Res. Anim. Sci. 36(3):159-163 (1999).
L. R. Arrington et al., Effects of Excess Dietary Iodine Upon Pullets and Laying Hens. J. Nutr. 92:325-330 (1967).
L. G. Barron et al., Plasma Lipoprotein Changes in Hens (*Gallus domesticus*) During an Induced Molt. Comp. Biochem. Physiol. B. Biochem. Mol. Biol. 123(1):9-16 (1999).
D. Bell, Characteristics of Force-Molted Flocks. Feedstuffs 37(17):46-48 (1965).
D. D. Bell, Historical and Current Molting Practices in the U.S. Table Egg Industry. Poult. Sci. 82:965-970 (2003).
W. D. Berry, The Physiology of Induced Molting. Poult. Sci. 82:971-980 (2003).
P. E. Biggs et al., Evaluation of Nonfeed Removal Methods for Molting Programs. Poult. Sci. 82:749-753 (2003).
P. E. Biggs et al., Further Evaluation of Nonfeed Removal Methods for Molting Programs. Poult. Sci. 83:745-752 (2004).
J. P. Bilezikian et al., Induction of Sustaine Hyperthyroidism and Hypothyroidism in the Turkey: Physiological and Biochemical Observations. Poult. Sci. 59:628-634 (1980).
R. M. Blakely and R. W. Anderson, Studies with Rape-seed Oilcake Meal. II. The Effect of the Inclusion of Protamone in the Diet . . . Can. J. Agric. Sci. 28:398-402 (1948).
K. L. Blaxter, The Preparation and Biological Effects of Iodinated Proteins. 4. The Effect of Iodinated Protein Feeding on the Lactating .. J. Endocrinol. 4:266-299 (1945).
K. L. Blaxter et al., The Role of Thyroidal Materials end of Synthetic Goitrogens in Animal Production and an Appraisal of Their Practical . . . J. Anim. Sci. 8:307-352 (1949).
M. A. Boone et al., Thyroid Studies in Fast and Slow Feathering Rhode Island Red Chicks. Poult. Sci. 29:195-200 (1950).
J. Brake et al., Physiological Changes in Caged Layers During a Forced Mott. 3. Plasma Thyroxine, Plasma Triiodothyronine, Adrenal . . . Poult. Sci. 58:1345-1350 (1979).
R. Braw-Tal et al., Hormonal Changes Associated With Aging and Induced Molting of Domestic Hens. Br. Poult. Sci. 45(6):815-822 (2004).
W. H. Burke and Y. A. Attia, Molting Single Comb White Leghoms With the Use of the Lupon Depot Formulation of Leuprolide Acetate. Poult. Sci. 73:1226-1232 (1994).
L. J. Cole and F. B. Hutt, Further Experiments on Feeding Thyroid to Fowl. Poult. Sci. 7:60-66 (1928).
E. Decuypere and G. Verheyen, Physiological Basis of Induced Molting and Tissue Regeneration in Fowls. World's Poult. Sci. 42(1):56-68 (1986).
R. Groscolas end J. Leloup, The Endocrine Control of Reproduction and Molt in Male and Female Emperor (*Aptendodytes forsteri*) . . . Gen. Comp. Endocrinol. 63:264-274 (1988).
R. H. Harms et al., Influence of Protamone on Fatty Liver Syndrome in Commercial Laying Hens. Poult. Sci. 61:2370-2374 (1982).
R. Hemken, Iodine. Anim. Nutr. & Health 36(1)12-14 (1981).
M. Herremans, Age and Strain Differences in Plumage Renewal During Natural and Induced Moulting of Hybrid Hens. Br. Poult. Sci. 29(4):825-835 (1988).
B. A. Herbert and C. C. Brunson, The Effects of Diethyistilbestrol, Testosterone, Thiouracil, and Thyroprotein on the Chemical Composition . . . Poult. Sci. 36:898-904 (1957).
J. A. Herbert and G. J. Cerniglia. Comparison of Low Sodium Chloride, High Zinc Oxide and High Potassium Iodide for Force Pausing Layers. Poult. Sci. 58:1015 (1979).
K. Himeno and Y. Tanabe, Mechanism of Molting in the Hen. Poult. Sci. 36:835-842 (1957).
P. S. Holt, Molting and *Salmonella* enterica Serovar enterldltis Infection: the Problem and Some Solutions. Poult. Sci. 82:1008-1010 (2003).
D. M. Hooge, Beneficial Responses to Levothyroxine and Other Thyroxinic Substances in Avian Species. U.S. Appl. No. 60/586,104. 34 pp. Jul. 7, 2004.

(Continued)

*Primary Examiner* — Kevin E Weddington

(57) ABSTRACT

A method is disclosed which is useful for elevating blood thyroid hormone levels in avian species (especially poultry species such as chickens, turkeys, ducks, quail, etc.) by implantation, injection, or supplementation of feed or water with thyroid hormones or thyroid-active substances (e.g., L-thyroxine, triiodothyronine, defatted and dessicated thyroid) to induce molting in order to extend egg production.

7 Claims, No Drawings

OTHER PUBLICATIONS

S. Hoshino et al., Changes in Plasma Thyroid Hormones, Lutenizing Hormone (LH), Estradiol, Progesterone and Corticosterone of . . . Comp. Biochem. Physiol, 90A:355-359 (1988).

M. R. Irwin et al., Effect of Feeding Thyroactive Iodocasein on Growth, Feathering and Weights of Glands of Young Chicks. Poult. Sci. 22:374-380 (1943).

A. L. Johnson and J. Brake, Zinc-Induced Molt: Evidence for a Direct Inhibitory Effect on Granulosa Cell Steroidogenesis. Poult. Sci. 71:161-167 (1992).

K. Keshavarz and F. W. Quimby, An Investigation of Different Molting Techniques with an Emphasis on Animal Welfare. J. Appl. Poult. Res. 11:54-67 (2002).

S. Kobayshi et al., Substrate Specificity of Iodothyronine 5'-Deiodinase in Rat Liver Homogenates and Its Requirements of Divalent . . . Life Sci. 38(24):2231-2238 (1988).

J. M. Koch et al., Melengestrol Acetate (MGA) as an Alternative Method to Induce Molting in Hens. Poult. Sci. 83(Suppl. 1):152 (2004).

I. L. Kosin and W. Wakely, The Effect of Iodinated Casein on Molting in Turkeys. Poult. Sci. 27:670-671 (1948).

W. J. Kuenzel et al., A Practical Method for Induced Molting of Caged Layers That Combines Full Access to Feed and Water . . . World's Poult. Sci. J. 61:in press (2005).

W. J. Kuenzel, Neurobiology of Molt in Avian Species. Poult. Sci. 82:981-991 (2003).

R. J. Lien and T. D. Siopes, Effects of Short-Term Thyroxine Administration During the Laying Period on Egg Production and Moulting . . . Br. Poult. Sci. 34(2):405-416 (1993).

R. J. Lien and T. D. Siopes, Turkey Plasma Thyroid Hormone and Prolactin Concentrations Throughout an Egg Laying Cycle and in Relation . . . Poult. Sci. 68:1409-1417 (1989).

B. F. Miller et al., The Effect of Thyroxine on Egg Production and Egg Quality on Normal and Radio-Thyroid-Ecrecticized Hens. Poult. Sci. 41:989-994 (1962).

W. S. Newcomer, Thyroxine and Triiodothyronine in Blood After Ingestion of Iodinated Casein by Chicks. Poult. Sci. 55:60-69 (1976).

R. K. Noles, Subsequent Production and Egg Quality of Forced Molted Hens. Poult. Sci, 45:50-57 (1966).

M. M. Oloufa, Effect of Thyroprotein on the Growth of Egyptian Chicks. Poult. Sci. 34:1292-1294 (1955).

R. Otsuka et al., Changes in Circulating LH, Sex Steroid Hormones, Thyroid Hormones and Corticosterone in Relation to Breeding . . . Zoolog. Sci. 15(1)103-109 (1998).

J. Parker, Influence of Thyroactive Iodocasein by Chicks. Proc. Soc. Exp. Biol, Med. 52:234-236 (1943).

J. T. Perdamo et al., Effect of Dietary Iodine Upon Egg Production, Fertility and Hatchability. Proc. Soc. Exp. Biol. Med. 122:758-760 (1966).

P. Pitt-Rivers and S. S. Randall, The Preparation and Biological Effects of Iodinated Proteins. 2. Preparation and Properties of . . . J. Endocrinol. 4:221-236 (1945).

E. P. Reineke and C. W. Turner, Formation in Vitro of Highly Active Thyroproteins, Their Biologic Assay, and Practical . . . Missouri Agr. Exp. Sta. Res. Bull. 355:1-88 (1942).

E. P. Reineke and C. W. Turner, The Effect of Manganese Compounds and Certain Other Factors on the Formation of Thyroxine in Iodinated . . . J. Biol. Chem. 161:613-619 (1945).

E. P. Reineke et al., The Effect of Progressive Iodination Followed by Incubation at High Temperature on the Thyroidal Activity . . . J. Biol. Chem. 147:115-119 (1943).

E. P. Reineke at al., The Effect of Progressive Iodination of The Thyroidal Activity of Iodinated Casien. J. Biol. Chem. 143:285-293 (1942).

R. H. Roberson and V. Trujillo, The Effect of Methionine, Thiouracll, Dinestrol Diacetate and Thyroprotein on Development and Prevention . . . Poult. Sci. 54:715-721 (1975).

K. Sekimoto et al., Thyroxine-Induced Molting and Gonadal Function in Laying Hens. Poult. Sci, 66:752-756 (1987).

L. S. Srivastava and C. W. Turner, Comparison of Biological Activity of Injected and Orally Administered L-thyroxine . . . Proc. Soc. Exp. Biol. Med. 126:157-161 (1967).

Z. Szelenyi and P. Peczely, Thyroxine Induced Molt in Domestic Hen. Acta. Physiol. Hung. 72(2):143-149 (1988).

K. Tona at al., Effect of Induced Molting on Albumen Quality, Hatchability, and Chick Body Weight from Broiler Breeders. Poult. Sci. 81:327-332 (2002).

H. B. Torrey and B. Horning, The Effects of Thyroid Feeding on the Molting Process and Feather Structure of the Domestic Fowl. Proc. Soc. Exp. Biol. Med. 19:275-279 (1922).

C. W. Turner et al., Effect of Feeding Thyroactive Iodocasein to Barred Rock Cockerels, Poult. Sci. 23:242-248 (1944).

C. W. Turner et al., Effect of Thyroid Hormone on Egg Production of White Leghorn Hens. Poult. Sci. 24:171-186 (1945).

C. W. Turner et al., The Effect of Thyroprotein on Egg Production. Poult. Sci. 24:522-523 (1945).

United States Registered Trademark, Protamone [Iodinated Casein], Serial No. 71475528, Reg. Apr. 3, 1945, 2nd Renewal Sep. 17, 1998; Agri-Tech, Inc., Kansas City, MO.

G. Verheyen et al., Dissociation of the Role of Thyroxine and Triiodothyronine in Relation to Egg Laying Arrest in Hens. Gen. Comp. Endocrinol. 53:499A (1984).

A. B. Webster, Physiology and Behavior of the Hen During Induced Molt. Poult. Sci. 82:992-1002 (2003).

R. S. Wheeler and E. Hoffmann, The Value of Thyroprotein in Starting, Growing and Laying Rations. II. The Growing Period . . . Poult. Sci. 27:509-514 (1948).

R. S. Wheeler et al., The Value of Thyroprotein in Starting, Growing and Laying Rations. I. Growth, Feathering, and Feed . . . Poult. Sci. 27:103-111 (1948).

R. W. Wideman et al., A Practical Method for Induced Molting of Caged Layers That Combines Full Access to Feed and Water . . . Report to United Egg Producers, 58 pp. (2004).

H. R. Wilson et al., Abdominal Fat Pad Reduction in Broilers with Thyroactive Iodinated Casein. Poult. Sci. 62:811-818 (1983).

H. R. Wilson et al., Performance of Hens Molted by Various Methods. Poult. Sci. 46:1406-1412 (1967).

J. H. Wolford et al., Reproductive Response of Laying Hens to Corticosterone Feeding. Poult. Sci. 62:1525 (1983).

J. H. Wolford, Induced Moulting in Laying Fowls. World's Poult. Sci. J. 40:66-73 (1984).

B. Zavadovsky, The Effect of Feeding Fowls on Thyroid Gland. Endocrinol, 9:125-136 (1925).

* cited by examiner

METHODS FOR IMPROVED AVIAN PERFORMANCE

CROSS-REFERENCE TO RELATED APPLICATION

This application claims priority on the basis of U.S. provisional application 60/586,104, filed Jul. 7, 2004, which application is hereby incorporated in its entirety by reference.

DESCRIPTION OF THE INVENTION

As a preliminary matter, the following definitions are offered in order to provide the reader an aid in understanding the teachings of the specification. These definitions are not intended to limit the scope of the claims nor to contradict any external authority but rather are intended strictly to assist the reader in discerning the meaning of applicant's disclosure.

Avian species—all birds, including poultry.

Basal metabolic rate—rate of cellular metabolism (as evidenced by heat production) and its associated oxygen consumption; the major regulatory function of thyroid hormones.

Bird—any warm-blooded vertebrate of the class Aves, having a body covered with feathers, bipedal locomotion (2 legs), and forelimbs modified into wings.

Diet, feed, or ration—any composition, compound, preparation, or mixture suitable for, or intended for, consumption by animals; usually distinguished from an additive, supplement, or premix.

Iodine (iodide)—a nonmetallic, halogen element essential in nutrition, being especially abundant in the colloid of the thyroid gland (i.e., the result of "iodine trapping" by the thyroid tissue).

Molting—1) as it refers to avian species, a physiological process associated in nature with short day length and involving reduced feed intake, body weight loss, regression of reproductive organs in females (ovaries and oviduct) and reproductive quiescence in males, and feather shedding and regrowth; 2) also the name of a procedure (i.e., forced molting or induced molting) used in the commercial poultry industry to rest the birds and extend the production of table eggs or fertile hatching eggs; heretofore, usually accomplished by 6-10 hour days and feed withdrawal (fasting) or feed and water withdrawal.

Poultry—domesticated birds raised primarily for meat, egg, and/or feather production such as chickens, turkeys, ducks, geese, guinea fowl, pigeons, pheasants, quail, other game birds, ostriches, emus, swans, peafowl, and so on.

Thyroid—1) gland which produces thyroid hormones, thyroxine ($T_4$; containing 4 iodine atoms) and triiodothyronine ($T_3$; containing 3 iodine atoms); and 3) a pharmaceutical substance derived from thyroid glands obtained from domesticated animals used for food by man, the glands having been deprived of connective tissue and fat, and then cleaned, dried, and powdered for use in replacement therapy. Note that monoiodotyrosine (MIT or $T_1$) and diiodotyrosine (DIT or $T_2$) also produced in the thyroid are not hormonally active.

Thyroid function status—euthyroid is normal; hyperthyroidism indicates excess production of thyroid hormones, and "hypothyroidism" signifies under-production of thyroid hormones.

Thyroxine—a crystalline iodine-containing compound, 3,5,3',5'-tetraiodothyronine, possessing the physiological properties of thyroid extract, used in treatment of hypothyroidism; formula is $C_{15}H_{11}I_4NO_4$, molecular weight is 776.8768, and iodine content is 65.3408% because iodine is relatively heavy with an atomic weight of 126.9044.

Thyroxinic—containing thyroxine, as in the term "thyroxinic substance"

Triiodothyronine—one of the compounds liberated from thyroglobulin by hydrolysis (3,3',5-triiodothyronine); reverse $T_3$ is 3,3',5'-triiodothyronine (sometimes written $rT_3$).

Thyroprotein or Thyroactive Iodinated Casein—thyroprotein can be produced from any tyrosine-containing proteins; as distinguished from simply iodinated casein which can contain monoiodotyrosine and diiodotyrosine (one phenyl ring with 1 or 2 iodine atoms), thyroactive iodinated casein, occasionally abbreviated herein as TIC (e.g., Protamone®, Agri-Tech, Inc., Kansas City, Mo., no longer marketed), has biphenyl ether derivatives with triiodothyronine ($T_3$) and thyroxine ($T_4$) activities by analysis such as by enzyme hydrolysis and HPLC.

Thyroactive iodinated organic compound—a categorical term for any organic compound having iodine as an integral component and having thyroid hormone activity (e.g., L-thyroxine content by HPLC analysis).

That preliminary matter now being concluded, the following background and description are accordingly provided.

a. Molting in the Commercial Egg Industry (Table Eggs).

Induced molting of caged laying hens is crucial for the profitability of the table egg industry to extend egg production and improve shell quality (Bell, 1965; Noles, 1966; Wolford, 1984; DeCuypere and Verheyen, 1986; Kuenzel, 2003). Bell (2003) estimated that more than 75% of all commercial laying hen flocks in the U.S. are molted as part of a regular replacement program. Today, there are about 300 million caged laying hens in the U.S. However, in response to animal welfare and public relations considerations, McDonald's and Wendy's, as well as the American Veterinary Medical Association and United Egg Producers, have adopted policies designed to compel discontinuation of commonly used molting techniques that are based on feed and water withdrawal, or that cause feed avoidance. Holt (2003) stated that induced molting by the conventional feed removal (fasting) method depresses the immune system and exacerbates a *Salmonella enteritidis* problem.

Several low nutrient density feed molting programs have been developed recently, but cessation of egg production tends to be variable and incomplete (Biggs et al., 2004). Koch et al. (2004) reported that 4 or 8 mg melengestrol acetate (MGA), a progestin, per laying hen per day through the feed results in reversible regression of the reproductive system; perhaps 10 to 15 mg MGA daily may be required for complete cessation of egg production (0%). Szelenyi et al. (1988) induce forced molt in hens with 5 mg progesterone/day for 25 days, and feathers were shed between days 11 and 19. Johnson and Brake (1992) observed that 2,800 mg zinc/kg diet had an inhibitory action on progesterone production in F1 granulosa cells of the ovary in laying hens. Kobayashi et al. (1986) determined that zinc ion appeared to be a potent inhibitor in both $T_4$ and $rT_3$ deiodination systems in rat liver homogenates, possibly indicating a $T_4$ sparing effect by zinc. Burke and Attia (1994) dosed White Leghorn hens with a single i.m. injection of Lupron Depot® (Abbott Labs, N. Chicago, Ill.) formulation of leuprolide acetate, a luteinizing hormone-releasing hormone agonist, designed to release 60 mcg/kg body weight per day for 30 days and egg production dropped to 3.5% in the second week with no body weight loss. Braw-Tal et al. (2004) found a very sharp rise in corticosterone, an indicator of stress, after 2 days on molting treatments such as feed withdrawal or moderate zinc and low calcium, and 20 to 40 mg corticosterone/kg diet has been shown to cause cessation of egg production in 4 to 8 days in 98% of laying hens (Wolford et al., 1983). Barron et al. (1999) deprived laying hens of light for 48 hours, followed by 8 hours of light daily, and withdrew feed from day 0 but allowed access to distilled water and oyster shell. Egg production ceased in an average of 3.2 days.

The cessation of egg production triggered by 5,000 mg iodide/kg diet is not accompanied by regression of mature ovarian follicles (although ovulation evidently ceased), and the extent of actual feather loss is minimal in young pullets whereas a typical molt response occurs in older hens (Perdamo et al., 1966; Arrington et al., 1967; Wilson et al., 1967; Herbert and Cemiglia, 1979; Albuquerque et al., 1999). The biological basis for the response of hens to 5,000 mg iodide/kg feed remains unclear.

Dramatic increases in the circulating levels of $T_4$ have been correlated with the normal molting process in a variety of avian species (Brake et al., 1979; DeCuypere and Verheyen, 1986; Groscolas and Leloup, 1986; Hoshino et al., 1988; and Kuenzel, 2003). Experiments have shown that feeding or injecting hens with thyroactive materials (more specifically $T_4$, tetraiodothyronine, rather than $T_3$, triiodothyronine) causes molting (feather loss) accompanied by cessation of egg production (Torrey and Homing, 1922; Zavadovsky, 1925; Cole and Hutt, 1928; Blaxter et al., 1949; Himeno and Tanabe, 1957; Verheyen et al., 1984; DeCuypere and Verheyen, 1986; Sekimoto et al., 1987; and Keshavarz and Quimby, 2002). Feeding diets containing thyroactive iodinated casein (1,400 mg/kg) to turkeys failed to cause young (25 week old) hens to molt but induced molt in older (yearling) turkey hens when fed over a period of 3 weeks (Kosin and Wakely, 1948).

Miller et al. (1962) found when injecting 9 to 729 micrograms L-thyroxine/100 g body weight (with injections started on 3 different weeks and discontinued once the highest thyroxine level was reached, 9 mcg/100 g body weight intitially in the leg and the level tripled each week to maximum 729 mcg/100 g body weight) to White Leghorn hens 7 months of age. Excessive levels of injected thyroxine (e.g., 243 micrograms/100 g body weight) caused cessation of egg production and rapid molt, with 47% mortality, but egg weight was unaffected. Two key studies more recently clearly demonstrated that intramuscular injections of 500 to 700 μg of $T_4$ per kg body weight per day caused egg production to cease completely within 3 to 7 days (DeCuypere and Verheyen, 1986; Sekimoto et al., 1987). Szelenyi and Peczely (1988) treated laying hens with 0.2 or 0.4 mg thyroxine per hen for 21 consecutive days in two identical experiments and observed that: 1) the lower dose diminished egg production but did not result in molting, and 2) the higher dose stopped egg laying on the 16th day and caused a loss of contour feathers from the 14th day onward. The new plumage was completely developed in the latter group on or about the 42nd day from initial treatment.

When animals consume and digest the iodinated proteins, free $T_4$ (as well as $T_3$) is liberated and absorbed into the blood stream. For example, iodinated casein (formerly marketed as Protamone®) contained approximately 1% $T_4$ by weight, and provided a biologically effective source of supplemental thyroxine when fed to cows and chickens (Reineke and Turner, 1942; Irwin et al., 1943; Parker, 1943; Turner et al., 1944, 1945a, 1945b; Blaxter, 1945; Blakely and Anderson, 1948; Wheeler and Hoffman, 1948; Wheeler et al., 1948; Blaxter et al., 1949; Boone et al., 1950; Oloufa, 1955; Herbert and Brunson, 1957; Srivastava and Turner, 1967; Roberson and Trujillo, 1975; Newcomer, 1976; Harms et al., 1982; Wilson et al., 1983). Serum $T_4$ levels increased by >25% within two days after White Leghorn cockerels began consuming diets supplemented with 0.02 or 0.04% levels of Protamone® (Newcomer, 1976). Whether injected or administered orally, the effects of thyroactive iodinated casein were shown to be qualitatively similar to those of L-thyroxine ($T_4$) in poultry (Srivastava and Turner, 1967).

Turner and Reineke, Sep. 18, 1945, stated that "the administration of iodinated protein to birds in amounts substantially less than we recommend has little or no effect, while the administration of amounts substantially greater actually causes a decrease in growth and egg production". In a trial with 2-year old laying hens, the chickens were fed thyroactive iodinated casein at levels of 0, 0.01, 0.022, or 0.04% in the diet (lots 1-4). It was observed that "hens moulted shortly after being placed in the laying batteries but the birds receiving the iodinated protein all molted at once and much more rapidly than the untreated birds. During the moult the egg production of the birds in lots 2, 3, and 4 dropped below the egg production of the controls in lot 1. However, after moulting the egg production of the hens receiving the iodinated protein rapidly passed the egg production of untreated controls. This was particularly true of birds in lots 2 and 3. The egg production of the birds in lot 3 was outstanding [0.022% level or 220 ppm]." They further stated that "preliminary tests using [a dietary supplemental level of 0.22%] iodinated protein . . . caused marked decreases in body weight of birds and [0.077%] iodinated protein . . . depressed egg production over periods of months". The authors discussed the toxicity of thyroxine and described molting in hens resulting from consumption of excessive dietary thyroactive iodinated casein, implying that this was a danger to be avoided. They failed to realize its benefits or make any claim regarding molting in commercial flocks.

Keshavarz and Quimby (2002) evaluated the feasibility of molting 66-week-old caged laying hens with a supplement of 10 mg thyroxine/kg feed to either 96.6% corn or 91.3% grape pomace based diets, compared to traditional feed withdrawal molting. Thyroxine was added to accelerate the rate of body weight loss and to reduce the period needed to reach 30% body weight loss. A 1-day feed withdrawal, followed by grape pomace diet plus thyroxine, for inducing molt resulted in similar days to target body weight as the conventional feed withdrawal method (16 days vs 14 days, respectively) and caused similar regression of ovaries and oviduct. The 1-day fast or no fast followed by corn diet with or without thyroxine all required 28 days. The feed withdrawal control hens had 66.8% egg production from 66 to 98 weeks whereas the grape pomace diet plus thyroxine hens had 64.7% followed by corn diet plus thyroxine hens with 57.1 to 60.2%. This 10 mg thyroxine/kg of diet level was insufficient to induce a rapid cessation of egg production within 3 to 10 days, and the 1-day feed withdrawal required prior to feeding grape pomace diet plus thyroxine is now considered unfriendly with regard to animal welfare. The 10 mg/kg level of thyroxine supplementation helped reduce but did not entirely eliminate egg production, nor did it cause satisfactory regression of the reproductive tract unless coupled with feed withdrawal or substantial nutrient restriction. These researchers used 10 mg thyroxine/kg feed for its catabolic and heat production functions to hasten body weight loss, not to induce molt. They failed to make the critical discovery of optimum level needed to induce molting entirely with exogenous thyroid hormone and without feed withdrawal molting.

Therefore, L-thyroxine supplementation to complete, nutritionally well-balanced feed to induce molting is desirable. An "animal welfare friendly" molting program allowing full access to treated feed and to drinking water is beneficial for disease prevention, mortality reduction, and maintaining good relationships with egg consumers. The present invention surprisingly provides L-thyroxine as the natural hormone most closely associated with molting and that administering a dietary level of approximately 10 to 500 mg L-thyroxine/kg (preferably about 40 mg/kg; alone on in combination with triiodothyronine as in thyroactive iodinated casein) consistently induces cessation of egg production, body weight loss, and feather molt typical of molting by feed withdrawal or natural short day length, in females of avian species. Reduced feed and calcium intake due to 40 mg thyroxine/kg diet is correctable to some extent by feeding the thyroxine treated feed on alternate days although this slows the molt induction process. Preconditioning hens with short day length (e.g., 7-10 days of 10 hours light daily), using short day length during the molt induction period, and offering low nutrient density diets with about 2% calcium facilitate the molting process.

b. Molting Other Poultry and Avian Species

Tona et al. (2002) described experiments molting commercial Cobb broiler breeder hens, 55 to 62 weeks of age. Molting increased egg internal quality (Haugh units) and hatchability of eggs compared to unmolted controls. Herremans (1988) reported from molting studies with white- and brown-egg layers and with broiler breeder hens that "at comparable age the moulting response was considerably more extensive in broiler-breeders than in layers". However, Hemken (1981) stated that adding iodine at 50 mg/kg to breeder hen diets caused a reduction in hatchability of eggs. Therefore, hatchability of fertile eggs from hens during $T_4$ molting treatment is monitored for iodine content, and these may have to be diverted to other uses such as human consumption (150 mcg/egg maximum) or rendering.

Bilezikian et al. (1980) found that 3 mcg L-thyroxine/mL water (600 to 900 mcg/bird/day) to 20 to 25 week old turkey females caused hens to rarely lay eggs and shells were incompletely calcified; however, hypothyroid turkeys did not lay eggs either. Based on previous work by Lien and Siopes (1989) indicating that $T_4$ may be involved with photorefractoriness (insensitivity to light), Lien and Siopes (1993) dosed laying turkeys with 0.075 to 2 mg L-thyroxine/bird/day by intramuscular injection for either 2 or 3 weeks following 10 weeks of photostimulation to determine photorefractoriness, feed consumption, and degree of molting. Turkey hens in two trials were 40 and 72 weeks of age, respectively. Transient depressions in egg production and molting were observed during and after $T_4$ treatments. Feed consumption declined with increasing $T_4$ doses. Turkeys in the 2 mg L-thyroxine/hen/day treatment terminated egg production during $T_4$ treatment and remained out of production for 4 weeks after treatment. These turkeys treated for 3 weeks molted body feathers and most primary remiges. Thyroxine administration did not result in photorefractoriness (as in starlings and coturnix quail) because turkey hens came back into egg production. Injecting large numbers of turkey hens or adult females of other poultry species is economically infeasible due to the exorbitant labor expense. Pairs of Humboldt penguins at Tokyo Sea Life Park were reported by Otsuka et al. (1998) to molt around the end of July or early August (males usually started earlier), coincident with a sharp increase in plasma $T_4$ which doubled within 10 days and lasted for a month. Duration of feather molting was short, averaging about 13 days.

According to the present invention, L-thyroxine or thyroxine-containing (thyroxinic) substance is administered to adult females of avian species, preferably via the diet at approximately 40 mg/kg feed (10 to 500 mg/kg) to induce molting and extend egg production.

c. Conventional Methods of Making Thyroactive Iodinated Casein or Levothyroxine.

In the manufacture of thyroactive iodinated casein, although casein has on average about 5.0% tyrosine which could theoretically yield about 9.38% thyroxine, it actually yields about 1% on analysis. This calculation is based on the statement of Reineke and Turner (1945) that casein with 5.65% tyrosine (slightly high estimate) would have theoretical yield of 10.6% thyroxine.

IG Farbenindustrie AG (Patent No. GB492265, Sep. 13, 1938; Manufacture of Thyroxin), described manufacture of thyroxine from iodinated proteins by a hydrolytic decomposition, with the iodination carried out in weakly alkaline aqueous solution at moderately raised temperature by gradually adding finely pulverized iodine and stirring with a metal rod as catalyst, hydrolyzing the iodinated protein, and purifying the product. The Million test used for residual iodine contains mercury and is environmentally unfriendly.

Quaker Oats Co. and American Dairies Inc. (GB568183, Mar. 22, 1945, Thyroprotein Composition and Method of Making the Same; GB598679, Feb. 24, 1948, Improvements Relating to Processes for the Production of Thyroxine; GB598680, Feb. 24, 1948, Thyroprotein Composition and Method of Making the Same) detailed a method for manufacture of thyroprotein and improvements relating thereto. GB568183 included a mixture of iodine and potassium iodide in aqueous solution. In GB598679, L-thyroxine was obtained from thyroprotein compositions without racemization by hydrolyzing (refluxing together) in an aqueous solution of an acid and N-butyl alcohol and extracting substantially pure thyroxine. The acid may be a mineral acid such as hydrochloric acid, but preferably sulfuric acid. Patent GB598680 iodinated protein at 50 to 70° C. in an aqeous solution having a pH of 6.8 to 10 until a negative Million test, then at 50 to 100° C. for 12 to 72 hours with aeration, vigorous stirring, and in the presence of metal or peroxide catalysts. Increasing increments of iodine to protein were tested in relation to thyroxine output.

U.S. Pat. No. 2,329,445 (Turner and Reineke, Sep. 14, 1945) described Thyroprotein and Method for Making the Same. Skim milk could be replaced by: casein, milk albumin; blood serum, albumin, or globulin, egg albumin, meat meal or its protein, or other animal proteins; cottonseed meal, gluten meal, soybean meal, peanut meal, coconut meal or other high protein ingredients with low oil contents. Molecular iodine is preferred, but it can be replaced by salts of iodine such as NaI, KI, NaIO$_3$, or others capable of releasing free iodine. This and similar processes such as chlorination and bromination are well known in the art.

Turner and Reineke (Jul. 3, 1945), in U.S. Pat. No. 2,379, 842, Thyroprotein Composition and Method of Making the Same, stated that to obtain maximum thyroxine activity, only sufficient iodine is added to substitute 2 atoms of iodine per molecule of tyrosine (i.e., 4 to 6 atoms of iodine per molecule of tyrosine). Excess iodine next iodinates the imidazole ring of histidine, and then oxidizes tryptophan and part of the sulfur of the cysteine complex (cystine). The iodination of tyrosine proceeds by substitution according to the equation: Tyrosine+2I$_2$=diiodotyrosine+2HI.

Molting experiments. According to the present invention, thyroxine (T$_4$) is administered as natural molting hormone for avian species. Research was designed to provide the commercial egg industry with a "hen-friendly" induced molting program, that will satisfy animal welfare considerations, by dosing hens with L-thyroxine. The following experiments, 1 through 4, were made possible by a $20,000 grant from United Egg Producers and were conducted with caged laying hens (chickens): 1) to validate the concept that adequately increasing circulating thyroxine ($T_4$) can induce molting, 2) to determine the optimum dose, and 3) to evaluate effectiveness of different thyroxine sources. Other experiments were subsequently carried out with broiler breeder hens and roosters, caged laying hens, and turkey breeder hens to evaluate the responses of other breeds and classes of poultry to the "$T_4$ molt" to accomplish reproductive rejuvenation.

Experiment 1. Confirmation that Injected Thyroxine Induces Molting. The first study with 60-week old Hy-Line W-36 White Leghorn hens, not previously molted, lasted 40 days and was designed to confirm the efficacy of injecting $T_4$ from Na-L-thyroxine pentahydrate intramuscularly as a trigger for molting and cessation of egg production. While acknowledging that injecting individual hens is commercially impractical (Webster, 2003), nevertheless an initial study was needed to establish the efficacy of $T_4$ when it is delivered directly into the hens in precisely measured doses (Tables 1 and 2). The photoperiod was 17 hours of light per day (0330 hours to 2030 hours).

Egg production in the Saline Group remained unchanged throughout the injection and post-injection intervals (day 15 to day 40 inclusive), and injecting 250 μg $T_4$ per kg body weight for 12 consecutive days did not reduce egg production significantly. Egg production was significantly reduced 4 days after the start of injecting the 500 and 1,000 μg $T_4$ Groups, with egg production ceasing entirely in the 1,000 μg $T_4$ Group by the $8^{th}$ day of $T_4$ injection. A week after injections were terminated, several hens in the 500 μg $T_4$ Group resumed sporadic egg production whereas hens in the 1000 μg $T_4$ Group did not resume production for the remainder of the experiment. Injecting 2,000 and 4,000 μg $T_4$ per kg body weight for 3 consecutive days triggered a rapid and complete cessation of egg production within 6 or 4 days, respectively, which did not subsequently recover for the remainder of the experiment.

Two hens (2 of 8=25%) in the 1,000 μg $T_4$ Group died on the $9^{th}$ and $10^{th}$ day after the start of $T_4$ injection, and one hen (1 of 4=25%) in the 4000 μg $T_4$ Group died on the $8^{th}$ day after the start of $T_4$ injection. No mortality occurred in the remaining Groups throughout the experiment. None of the hens in the Saline group molted, and three hens in the 250 μg $T_4$ Group began to molt 10 to 15 days after the start of injections. In the 500 and 1,000 μg $T_4$ Groups, molting began in all cages on the $11^{th}$ and $9^{th}$ days, respectively, after the start of $T_4$ injection. For the 2,000 and 4,000 μg $T_4$ Groups, molting commenced in all cages on the $9^{th}$ day after the start of injection. In all Groups, molting hens shed virtually all feathers within 7 to 10 days, and during the subsequent week feather regrowth progressed equally well in all Groups.

Body weights did not differ among the Groups prior to the injections, and the Saline Group retained the same body weight throughout the experiment. However, $T_4$ injections significantly reduced the body weight of all Groups. Complete cessation of egg production was associated with a 15 to 25% reduction in body weight at the onset of molt, a percentage that includes the weight of feathers lost. There was an inverse relationship between the $T_4$ injection dose and daily feed intake, with feed intake being significantly lower in hens injected with $\geqq 500$ μg $T_4$ when compared with the Saline-injected controls. The sole behavioral observation in Groups receiving $T_4$ was that higher doses ($\geqq 1,000$ μg $T_4$ per kg BW per day) caused hens to be more excitable and "flighty" when taken from their cages for injections. Otherwise, no cannibalism or aggression was noted within or between cages. Once molting began the hens became less active and tended to remain sitting in their cages when humans entered the chamber.

Necropsies were conducted on the three birds that died (two from the 1,000 μg $T_4$ Group, one from the 4,000 μg $T_4$ Group) as well as four uninjected control hens, two hens from the 250 μg $T_4$ Group, two hens from the 500 μg $T_4$ Group, one hen from the 1,000 μg $T_4$ Group, and one hen from the 4,000 μg $T_4$ Group. There was no evidence that the repeated injections had damaged the breast muscle. Hens from the uninjected Control Group and 250 μg $T_4$ Group were well fleshed, had ample (Control Group) or appeared to have slightly reduced (250 μg $T_4$ Group) amounts of body fat, fully functional reproductive tracts, and ovaries containing typical hierarchies of 3 to 5 maturing follicles. A hard-shell egg was found in the shell gland of one hen from the 250 μg $T_4$ Group. Both hens in the 500 μg $T_4$ Group were molting, and their body fat was obviously reduced when compared with the Control and 250 μg $T_4$ hens. Both hens in the 500 μg $T_4$ Group had functional reproductive tracts including the presence of a partially calcified egg in the shell gland of one hen. The ovaries of both hens from the 500 μg $T_4$ Group had hierarchies of 3 or 5 maturing follicles. Hens in the 1,000 and 4,000 μg $T_4$ Groups were extremely lean, had completely regressed reproductive tracts ($\leqq 50\%$ normal size) and ovaries containing deteriorating (<4 mm diameter) or fully regressed/immature ($\leqq 2$ mm diameter) follicles. No obvious differences in thyroid sizes were observed among the Groups, the air sacs were clear in all hens examined, and no evidence of osteoporosis was detected.

TABLE 1

Hen-day egg production (%) beginning on day 14 at 2-day intervals by treatment; L-thyroxine administered by i.m. injection beginning on day 15 (for 12 days at 250 mcg level, 8 days at 500 or 1,000 mcg levels, and 3 days at 2,000 or 4,000 mcg levels) (Experiment 1).

| Dose, mcg/kg Body Wt | Day | | | | | | | | |
|---|---|---|---|---|---|---|---|---|---|
| | 14 | 16 | 18 | 20 | 22 | 24 | 26 | 28 | 30 |
| 0 (Saline) | 75.0 | 85.4 | 95.8 | 72.9 | 89.6 | 93.8 | 83.3 | 77.1 | 100.0 |
| 250 (12 d) | 93.8 | 87.5 | 68.8 | 56.3 | 25.0 | 31.3 | 37.5 | 31.3 | 37.5 |
| 500 (8 d) | 87.5 | 93.8 | 31.3 | 31.3 | 6.3 | 6.3 | 6.3 | 6.3 | 25.0 |
| 1,000 (8 d) | 81.3 | 68.8 | 31.3 | 12.5 | 0.0 | 0.0 | 0.0 | 0.0 | 0.0 |
| 2,000 (3 d) | 62.5 | 87.5 | 87.5 | 75.0 | 50.0 | 12.5 | 0.0 | 0.0 | 0.0 |
| 4,000 (3 d) | 62.5 | 87.5 | 100.0 | 87.5 | 25.0 | 0.0 | 0.0 | 0.0 | 0.0 |

Note:
There were 4 cages of 2 or 3 laying hens each per treatment group.

TABLE 2

Body weight, body weight change, and feed consumption by treatments (Experiment 1)

| Dose, mcg/kg Body Wt | Initial Body Weight, g | End of Injections Body Weight, g | Body Weight Change, g | Body Weight Change, % | Feed Intake, g/hen/day[1] |
|---|---|---|---|---|---|
| 0 (Saline) | 1448 | 1448 | 0 | 0 | 86.2 |
| 250 (12 d) | 1495 | 1300 | 195 | 13 | 58.7 |
| 500 (8 d) | 1472 | 1299 | 173 | 11 | 52.3 |
| 1,000 (8 d) | 1513 | 1167 | 347 | 23 | 31.4 |
| 2,000 (3 d) | 1510 | 1234 | 277 | 18 | 20.2 |
| 4,000 (3 d) | 1387 | 1165 | 222 | 16 | 11.7 |

[1]Feed consumption was measured from day 22 to day 28; see previous Table for injection days.

Experiment 2. Confirmation that Thyroxine Added to the Feed Induces Molting. The second study involved 102-week old Hy-Line W-36 White Leghorn hens (previously molted at 55 weeks old), lasted 30 days, and was designed to provide hens with $T_4$ (from Na-L-thyroxine pentahydrate) in the feed at sufficient levels to induce molting (e.g., loss of primary "flight" feathers), complete cessation of egg production, and full regression and involution of the reproductive tract (Tables 3-6). The photoperiod was 17 hours of light per day (0330 hours to 2030 hours).

The objective was to use $T_4$ to humanely induce molting in hens that are continuously provided with ad libitum access to palatable feed meeting or exceeding all National Research Council (1994) standards. Developing a fully efficacious yet affordable molting protocol was predicated on determining the minimum effective level for $T_4$ supplementation. Factors that potentially may affect the required level of $T_4$ supplementation include: (1) uncertainty regarding the efficiency of $T_4$ absorption by the gastrointestinal tract, (2) the possibility that continuous dietary ingestion of $T_4$ could trigger substantially different biological responses when compared single daily injections, and (3) the likelihood that daily $T_4$ intake would diminish in parallel with molt-related reductions in feed intake associated with cessation of egg production. A spontaneous and voluntary loss of appetite (anorexia) commonly accompanies seasonal molting and broodiness in a variety of avian species (Berry, 2003; Webster, 2003). Accordingly, the responses of hens to diets containing 10, 20, and 40 mg $T_4$/kg, to bracket the anticipated range of $T_4$ needed to cause an effective molt, were determined.

Egg production by the Control hens remained unchanged in both Chambers (i.e., exposed to either 6 or 10 days on test diets) throughout the 30-day experiment. Feeding 20 and 40 mg $T_4$/kg consistently reduced egg production within 4 days, whereas the 10 mg $T_4$/kg diet reduced egg production significantly only in Chamber 5 (6 days on test diets) but not in Chamber 6 (10 days on test diets). Removal of the test diets after 6 days caused sporadic egg production to resume at levels that were not lower than those of the Control group by day 18 in the 10 mg $T_4$ kg Group, and by day 20 in the 20 and 40 mg $T_4$/kg Groups, whereas feeding the 40 mg $T_4$/kg diet for 10 days caused egg production to cease completely for the duration of the experiment. No mortality occurred in any of the Groups throughout the experiment. None of the hens in the Control group molted, half of the hens in 10 mg $T_4$ kg Group in Chamber 6 (10 days on test diets) began to molt 11 days after $T_4$ feeding was initiated, and hens in the 20 and 40 mg $T_4$/kg Groups in both chambers molted 9 to 11 days after $T_4$ feeding was initiated. In Chamber 6 (10 days on test diets) the hens fed 40 mg $T_4$/kg shed virtually all feathers within 7 to 10 days, and feather re-growth during the subsequent week progressed well. Behavioral changes were not apparent in molting hens, regardless of the test diet or Chamber. No cannibalism or aggression was noted within or between cages of birds. The hens became sedentary after feather loss began.

The Control Groups in both Chambers retained their initial body weight throughout the experiment. All $T_4$ test diets caused progressive reductions in body weight, with absolute body weight tending to return toward the initial values after cessation of feeding the 10 and 20 mg $T_4$/kg diets. In the 40 mg $T_4$/kg Group both the body weight and percentage change in body weight consistently remained depressed until the end of the experiment. Reduction in the absolute hen-day feed intake and in the percentage change in hen-day feed intake paralleled the respective contemporaneous change in absolute body weight and percentage change in body weight. Thus, hens fed the 40 mg $T_4$/kg test diet for 10 days completely ceased egg production, shed virtually all of their feathers, reduced their feed intake by approximately 85%, and lost approximately 21% of their initial body weight. The percentage shell values did not change over time in the Control Group, but were similarly reduced within 4 days after the start of feeding the 10, 20, and 40 ppm $T_4$ test diets. Whole egg weights did not change during the 4 day period, averaging 65±1, 62±2, 65±2, and 65±3 g (mean±SEM) for the Control and 10, 20, and 40 ppm $T_4$ Groups, respectively. Necropsies were conducted on 12 hens that had entirely ceased egg production after being fed the test diets. Two hens appeared to be coming back into production because small (3 to 5 mm diameter) follicles were developing although the oviduct was fully regressed. The remaining hens were extremely lean, had completely regressed reproductive tracts ($\leq$50% normal size) and ovaries containing fully regressed and immature ($\leq$1 mm diameter) follicles.

TABLE 3

Hen-day egg production (%) beginning on day 4 at 2-day intervals by treatment; L-thyroxine administered in the diet at 0, 10, 20, 40 mg/kg on day 5 for either 6 or 10 days by room (Experiment 2).

| | Day | | | | | | | | | | | | | |
|---|---|---|---|---|---|---|---|---|---|---|---|---|---|---|
| Dose, mg/kg of feed | 4 | 6 | 8 | 10 | 12 | 14 | 16 | 18 | 20 | 22 | 24 | 26 | 28 | 30 |
| 0 (6 d) | 83 | 67 | 75 | 67 | 83 | 92 | 75 | 83 | 67 | 92 | 75 | 83 | 67 | 75 |
| 10 (6 d) | 75 | 58 | 25 | 8 | 17 | 0 | 33 | 25 | 58 | 75 | 83 | 42 | 83 | 75 |

TABLE 3-continued

Hen-day egg production (%) beginning on day 4 at 2-day intervals by treatment; L-thyroxine administered in the diet at 0, 10, 20, 40 mg/kg on day 5 for either 6 or 10 days by room (Experiment 2).

| Dose, mg/kg of feed | Day | | | | | | | | | | | | | |
|---|---|---|---|---|---|---|---|---|---|---|---|---|---|---|
| | 4 | 6 | 8 | 10 | 12 | 14 | 16 | 18 | 20 | 22 | 24 | 26 | 28 | 30 |
| 20 (6 d) | 94 | 69 | 17 | 0 | 17 | 14 | 33 | 39 | 47 | 64 | 64 | 78 | 89 | 61 |
| 40 (6 d) | 67 | 42 | 8 | 0 | 0 | 0 | 0 | 8 | 25 | 25 | 50 | 17 | 33 | 33 |
| 0 (10 d) | 92 | 92 | 92 | 67 | 83 | 92 | 75 | 75 | 75 | 67 | 67 | 92 | 83 | 75 |
| 10 (10 d) | 58 | 50 | 42 | 17 | 17 | 17 | 17 | 25 | 17 | 33 | 50 | 25 | 25 | 33 |
| 20 (10 d) | 75 | 58 | 8 | 8 | 0 | 0 | 0 | 8 | 8 | 17 | 17 | 17 | 33 | 25 |
| 40 (10 d) | 67 | 33 | 8 | 8 | 0 | 0 | 0 | 0 | 0 | 0 | 0 | 0 | 0 | 0 |

Note:
There were 3 cages of 2 hens each per treatment group.

TABLE 4

Body weight (BW) and body weight change (% BWC) from day 1 by thyroxine treatments, day 7 to day 30 (Experiment 2).

| Dose, mg/kg of feed | Day 1 | Day 7 | | Day 10 | | Day 14 | | Day 30 | |
|---|---|---|---|---|---|---|---|---|---|
| | BW, g | BW, g | % BWC | BW, g | % BWC | BW, g | % BWC | BW, g | % BWC |
| 0 (6 d) | 1532 | 1561 | 1.9 | 1529 | −0.2 | 1554 | 1.4 | 1586 | 3.5 |
| 10 (6 d) | 1501 | 1377 | −8.3 | 1293 | −13.9 | 1424 | −5.1 | 1483 | −1.2 |
| 20 (6 d) | 1582 | 1434 | −9.4 | 1373 | −13.2 | 1491 | −3.9 | 1521 | −3.9 |
| 40 (6 d) | 1629 | 1443 | −11.4 | 1350 | −17.1 | 1396 | −14.3 | 1481 | −9.1 |
| 0 (10 d) | 1421 | 1406 | −1.1 | 1421 | 0.0 | 1412 | −0.6 | 1426 | 0.4 |
| 10 (10 d) | 1477 | 1372 | −7.1 | 1335 | −9.6 | 1314 | −11.0 | 1400 | −5.2 |
| 20 (10 d) | 1680 | 1533 | −8.8 | 1431 | −14.8 | 1373 | −18.3 | 1448 | −13.8 |
| 40 (10 d) | 1572 | 1392 | −11.5 | 1309 | −16.7 | 1245 | −20.8 | 1322 | −15.9 |

Note:
Thyroxine treatment was added to diets on day 5.

TABLE 5

Feed consumption (FC, g/hen/day) and feed consumption change (% FCC) from days 2-4 by thyroxine treatments, including days 5-7, 8-10, and 11-14 (Experiment 2).

| Dose, mg/kg of feed | Days 2-4 | Days 5-7 | | Days 8-10 | | Day 11-14 | |
|---|---|---|---|---|---|---|---|
| | FC, g/hen/d | FC, g/hen/d | % FCC | FC, g/hen/d | % FCC | FC, g/hen/d | % FCC |
| 0 (6 d) | 100.7 | 97.7 | −3.0 | 88.7 | −11.9 | 98.0 | −2.7 |
| 10 (6 d) | 101.3 | 60.0 | −40.8 | 35.3 | −65.2 | 81.3 | −19.7 |
| 20 (6 d) | 103.0 | 42.0 | −59.2 | 33.7 | −67.3 | 73.7 | −28.4 |
| 40 (6 d) | 98.3 | 36.7 | −62.7 | 13.7 | −86.1 | 46.7 | −52.5 |
| 0 (10 d) | 108.3 | 101.3 | −6.5 | 91.0 | −16.0 | 102.0 | −5.8 |
| 10 (10 d) | 84.0 | 56.0 | −33.3 | 33.7 | −59.9 | 47.3 | −43.7 |
| 20 (10 d) | 120.7 | 54.7 | −54.7 | 30.0 | −75.1 | 32.7 | −72.9 |
| 40 (10 d) | 116.3 | 37.3 | −67.9 | 22.0 | −81.1 | 19.3 | −83.4 |

Note:
Thyroxine treatment was added to diets on day 5.

TABLE 6

Percent shell on eggs from thyroxine treatments; both rooms combined because of the limited number of eggs in some groups (Experiment 2).

| Dose, mg/kg of feed | Egg Shell, % (washed, dried) | | |
|---|---|---|---|
| | Days 2 to 4 | Days 5 to 6 | Days 7 to 8 |
| 0 (6 & 10 d) | 8.20 (n = 12) | 8.00 (n = 17) | 8.38 (n = 25) |
| 10 (6 & 10 d) | 7.93 (n = 6) | 7.39 (n = 9) | 6.63 (n = 8) |
| 20 (6 & 10 d) | 8.38 (n = 10) | 8.08 (n = 13) | 5.56 (n = 2) |
| 40 (6 & 10 d) | 8.34 (n = 6) | 7.82 (n = 6) | 6.63 (n = 3) |

Note:
Number of eggs sampled is n. Low calcium intake associated with low feed consumption for thyroxine-treated diets may largely be responsible for differences in egg shell %.

Experiment 3. Reducing the Photoperiod Minimally Enhances Molting Caused by Thyroxine Added to the Feed and Allows Response to Photostimulation Later. The third study was conducted with 96-week old Hy-Line W-36 White Leghorn hens (previously molted at 80 weeks of age) for 29 days to evaluate potential interactions between supplementing the feed with $T_4$ and reducing the photoperiod (8 hr vs 17 hr of light per day). The photoperiod remained at 16 h light/day throughout a previous study by Keshavarz and Quimby (2002) in which 10 mg $T_4$/kg was added to the feed. The photoperiod serves as the primary environmental signal that regulates reproductive function in many avian species. Increasing the photoperiod promotes maturation of the gonads and reproductive tract, whereas reducing the photoperiod causes the gonads and reproductive tract to regress and molting to occur. Reducing the photoperiod to $\leq$10 h/day during molting also tends to improve the post-molt performance of hens, presumably because the development of the ovaries and reproductive tract can be naturally photostimulated by gradually increasing the photoperiod as molted hens are brought back into lay (Berry, 2003). It is likely that photoperiod reduction will be used in commercial molting, either before (preconditioning), during, or after the molt treatment period, to permit response to post-molt photostimulation of the hens (DeCuypere and Verheyen, 1986; Hoshino et al., 1988; Biggs et al., 2003).

The experiment consisted of a 7-day acclimation period, 12 days of feeding the test diets, and 10 days of photoperiod adjustment (Reduced Daylength Group in Chamber 5 and Control group in Chamber 6). Reducing the photoperiod to 8 hours/day (0800 hours to 1600 hours) in Chamber 5 did not consistently reduce egg production or variability in egg production when compared with the initial 12 days for this group, or when compared with the Control group in Chamber 6 (17 hr light). Feeding 20 and 40 mg $T_4$/kg significantly reduced egg production within 4 days in Chamber 5 (8 hr light), and within 6 (40 mg $T_4$/kg) or 8 (20 mg $T_4$/kg) days in Chamber 6 (17 hr light). Only the hens fed the 40 mg $T_4$/kg diet in Chamber 6 (17 hr light) entirely ceased egg production for the remainder of the experiment whereas sporadic egg production continued by several hens in the other test diet groups. No mortality occurred in any of the Groups throughout the experiment. None of the hens in the Control groups or 20 mg $T_4$/kg groups molted in either chamber, 58% (7/12) of the hens in the 40 mg $T_4$/kg Group in Chamber 5 (8 hr light) molted fully (shed virtually all feathers within 7 to 10 days), and 100% of the hens in the 40 mg $T_4$ kg Group in Chamber 6 (17 hr light) molted fully. Feather regrowth subsequently progressed well in both 40 mg $T_4$/kg Groups, regardless of the ongoing difference in photoperiod. Behavioral changes were not apparent in molting hens, regardless of the test diet or Chamber. No cannibalism or aggression was noted within or between cages.

The Control Groups maintained or increased their body weight over the course of the experiment. All $T_4$ test diets caused reductions in body weight, with absolute body weight tending to return toward the initial values after cessation of feeding the test diets. Reduction in feed intake paralleled the respective contemporaneous changes in body weight. Thus, hens in Chamber 6 (17 hr light) that were fed the 40 mg $T_4$/kg test diet completely ceased egg production, shed virtually all of their feathers, reduced their feed intake by approximately 65%, and lost approximately 18% of their initial body weight. Hens in Chamber 5 (8 hr light) tended to have lower feed intake than hens in the respective Groups in Chamber 6 (17 hr light), presumably reflecting the impact of the reduced photoperiod (hours of light) on feed intake. Necropsies conducted at the end of experiment 3 revealed Group differences in ovary and oviduct weights that were consistent with contemporaneous egg production values. For example, the Control Groups in both chambers and the 20 mg $T_4$/kg Group in Chamber 6 (8 hr light) averaged between 50 and 60% hen-day egg production on day 34, and these groups also had the highest ovary and oviduct weights at the end of the experiment. In contrast, some hens in the 20 and 40 mg $T_4$/kg groups in Chamber 5 (8 hr light) continued to lay eggs sporadically, and all of the hens in the 40 mg $T_4$ kg group in Chamber 6 (17 hr light) ceased egg production entirely, as was reflected by proportional reductions in ovary and oviduct weights.

TABLE 8

Hen-day egg production (%) beginning on day 12 at 2-day intervals by treatment; L-thyroxine administered in the diet at 0, 20, 40 mg/kg on day 13 for 12 days with either 8 or 17 hour light (L) days by room (Experiment 3).

| Dose, mg/kg of feed | Day | | | | | | | | | | | |
|---|---|---|---|---|---|---|---|---|---|---|---|---|
| | 12 | 14 | 16 | 18 | 20 | 22 | 24 | 26 | 28 | 30 | 32 | 34 |
| 0 (8 hr L) | 85.4 | 60.4 | 79.2 | 81.3 | 56.3 | 72.9 | 56.3 | 93.8 | 70.8 | 64.6 | 54.2 | 58.3 |
| 20 (8 hr L) | 93.8 | 54.2 | 35.4 | 29.2 | 18.8 | 0.0 | 0.0 | 0.0 | 10.4 | 6.3 | 16.7 | 8.3 |
| 40 (8 hr L) | 83.3 | 66.7 | 16.7 | 8.3 | 12.5 | 4.2 | 8.3 | 4.2 | 4.2 | 8.3 | 4.2 | 8.3 |
| 0 (17 hr L) | 89.6 | 87.5 | 66.7 | 87.5 | 70.8 | 70.8 | 68.8 | 83.3 | 62.5 | 75.0 | 56.3 | 58.3 |
| 20 (17 hr L) | 91.7 | 58.3 | 35.4 | 31.3 | 14.6 | 27.1 | 4.2 | 18.8 | 0.0 | 29.2 | 41.7 | 54.2 |
| 40 (17 hr L) | 66.7 | 56.3 | 37.5 | 16.7 | 12.5 | 0.0 | 0.0 | 0.0 | 0.0 | 0.0 | 0.0 | 0.0 |

Note:
There were 4 cages of 3 hens each per treatment group.

TABLE 9

Body weight (BW) at day 12 (pre-molt), 22 (end of molt), and 34 (final) and body weight change (% BWC) from day 1 by thyroxine treatments in 8 or 17 hour daily light (L) rooms (Experiment 3).

| Dose, mg/kg of feed | Day 12 | Day 22 | | Day 34 | |
|---|---|---|---|---|---|
| | BW, g | BW, g | % BWC | BW, g | % BWC |
| 0 (8 hr L) | 1443 | 1436 | −0.5 | 1487 | 3.0 |
| 20 (8 hr L) | 1492 | 1301 | −12.8 | 1332 | −10.7 |
| 40 (8 hr L) | 1488 | 1222 | −17.9 | 1300 | −12.6 |
| 0 (17 hr L) | 1514 | 1480 | −2.2 | 1534 | 1.3 |
| 20 (17 hr L) | 1572 | 1363 | −13.3 | 1453 | −7.6 |
| 40 (17 hr L) | 1436 | 1178 | −18.0 | 1224 | −14.8 |

Note:
Thyroxine treatment was added to diets on day 13 for 12 days.

TABLE 9

Feed consumption (FC, g/hen/day) and feed consumption change (% FCC) from days 1-12, by thyroxine treatments in 8 or 17 hour daily light (L) rooms, including days 13-15, 16-22, and 30-34 (Experiment 3).

| Dose, mg/kg | Days 1-12 | Days 13-15 | | Days 16-22 | | Day 30-34 | |
|---|---|---|---|---|---|---|---|
| of feed | FC, g/hen/d | FC, g/hen/d | % FCC | FC, g/hen/d | % FCC | FC, g/hen/d | % FCC |
| 0 (8 hr L)  | 113.5 | 77.5 | −31.7 | 80.5  | −29.1 | 103.8 | −8.5  |
| 20 (8 hr L) | 121.3 | 41.8 | −65.5 | 44.5  | −63.3 | 82.5  | −32.0 |
| 40 (8 hr L) | 115.8 | 36.8 | −68.2 | 35.3  | −69.5 | 104.8 | −9.5  |
| 0 (17 hr L) | 110.0 | 94.0 | −14.5 | 103.0 | −6.4  | 138.5 | −25.9 |
| 20 (17 hr L)| 121.5 | 58.0 | −52.3 | 51.8  | −57.4 | 135.0 | 11.1  |
| 40 (17 hr L)| 103.3 | 42.0 | −59.3 | 37.5  | −63.7 | 93.3  | −9.7  |

Note:
Thyroxine treatment was added to diets on day 13 for 12 days.

TABLE 10

Ovary and oviduct weights per hen on day 34 as affected by previous dietary thyroxine treatments in 8 or 17 hour daily light (L) rooms (Experiment 3).

| Dose, mg/kg | Ovary Weight | | | Oviduct Weight | | |
|---|---|---|---|---|---|---|
| of feed | g | Std Dev | SEM | g | Std Dev | SEM |
| 0 (8 hr L)   | 38.54 | 8.53  | 2.70 | 52.84 | 6.52  | 2.06 |
| 20 (8 hr L)  | 7.91  | 13.98 | 4.42 | 18.64 | 21.97 | 6.94 |
| 40 (8 hr L)  | 9.32  | 16.32 | 4.71 | 14.25 | 19.62 | 5.66 |
| 0 (17 hr L)  | 45.99 | 8.16  | 2.46 | 59.95 | 7.45  | 2.25 |
| 20 (17 hr L) | 31.41 | 20.38 | 6.44 | 43.81 | 24.78 | 7.84 |
| 40 (17 hr L) | 3.82  | 2.86  | 0.86 | 8.03  | 3.08  | 0.93 |

Note:
The thyroxine treatment (molt) period was 10 days followed by 24 days on control feed, ending the study on day 34.
Std Dev is standard deviation, and SEM is standard error of mean.

Experiment 4. Thyroactive Iodinated Casein Feeding Trial. Twenty of these HyLine W36 SCWL hens (60 wk old) were housed at one hen per cage in Chambers 5 and 6 of the Poultry Environmental Research Laboratory on the University of Arkansas Poultry Research Farm. The photoperiod was 18 hours/day and the temperature was 75° F. (24° C.) throughout this experiment. All cages were equipped with low-pressure nipple waterers and the hens were provided ad libitum a mash-type corn-soy-based layer diet formulated by the University of Arkansas Poultry Feed Mill. Daily egg production was recorded by cage for the duration of the experiment. Non-laying hens were culled during the acclimation period, leaving 14 active layers. Three of these hens remained on the Control feed throughout the experiment and, depending on the quantity of iodinated casein produced in batches 2 to 5, the remaining hens received feed blended with iodinated casein for 7 to 25 days (see below). Hens that had not died before the end of the experiment the hens were euthanized with $CO_2$ gas.

Five batches of thyroactive iodinated casein were prepared using a "consensus" recipe based on methods described by Reineke and Turner (1942), Reineke et al. (1943), and Pitt-Rivers and Randall (1945). Batch #1 started with a pH that was too alkaline (>12), and the resulting material had a plastic-like consistency that solidified into an extremely hard and brittle mass. This batch was not fed to chickens. Batches 2 to 5 represented minor modifications using "KI" as an iodine source (Batches 2, 4, 5), or purified "I" as the iodine source (Batch 3). After each product was isolated, dried, and weighed, it then mixed at 1 part iodinated casein product to 2 parts (by weight) of standard laying hen diet. Feed mixed with batches 2 to 5 were fed to one or more hens.

The recipe that can be prepared in a 20-L plastic container shaped to fit into a laboratory water bath, and that can be used with confidence to molt SCWL hens is summarized as follows.

Consensus Recipe for Iodinated Casein a. Mix 14 L of distilled H2O with 3.325 g $MnSO_4.H_2O$ and 315 g of $NaHCO_3$. Dissolve with stirring and bring the solution up to the water bath temperature of 39° C. The initial pH should be approximately 8.00.

b. With stirring (a length of copper tubing was used as a manual stirring rod throughout) blend in 945 g Casein (Erie Foods International, Inc., Erie Ill. 61250. Edible Casein, CAS#9000-71-9) without allowing clumps or foam to develop. The pH should be in the range of 7.00 to 7.20. [NOTE: This is 2× the proportion of casein: water used by the primary reference sources, but is designed to maximize the product produced in small volume lab batches.]

c. Stir in 173.25 g of "KI" (VWR Scientific No. VW5225-5; FW 166.00) or 132.3 g of "I" (E. M. Science No. IXO 126/2 Iodine USP, FW 126.90). Add the iodine source gradually with occasional stirring over the course of 2 hours. When dissolved, the pH should be between 7.20 and 7.30. Note: These proportions of added iodine represent approximately 14% I by weight of casein, as per the recommendations of Reineke et al. (1942, 1943).

d. Raise the temperature to 70° C. and incubate with occasional stirring for 20 hours. The pH should increase to >8.00 after 8 hours, and to ≧9.00 at the end of this 20 hour incubation.

e. Titrate with glacial acetic acid and continuous stirring until the protein flocculates and floats to the surface. Keep titrating with more acid and periodically scoop off the floating material and drain on cheese cloth or cotton cloth. When all the protein has been precipitated, pour the remaining liquid through cloth to harvest the dispersed material. Consolidate the material in one lump, wrap it in cloth, squeeze out all excess liquid, then break up the resulting cake into fine particles for drying.

f. Dry at 50° C. overnight in a forced-air oven. Periodically break up the material into very fine particles as it dries.

g. Weigh the dry product. Actual dry weight for Batch 5 using "KI" was 912.55 g. This was mixed with 1,825.1 g feed (laying hen diet), and run in 200 g batches through a Waring blender to mix. The 200 g batches then were blended together and remixed to achieve homogeneity.

TABLE 11

Egg production records for individual hens that remained on control feed (C; n = 3 hens) or that received dietary thyroactive iodinated casein (TIC) from batches 2 (n = 1), 3 (n = 3), 4 (n = 2), and 5 (n = 5); number 1 indicates an egg was laid on that day (Experiment 4).

| Hen No. | 14 Days (Control Feed) | | | | | | | TIC Batch |
|---|---|---|---|---|---|---|---|---|
|  | −14 | −12 | −10 | −8 | −6 | −4 | −2 |  |
| 5  | 1 | 1 | 1 | 1 | 1 | 1 1 | 1 1 1 | 1 1 | 5 |
| 6  | 1 | 1 | 1 |   | 1 |   | 1 | 1 1 1 1 1 | 5 |
| 7  | 1 | 1 | 1 | 1 | 1 | 1 1 | 1 1 1 | 1 | 5 |
| 8  |   | 1 | 1 |   | 1 | 1 1 |   | 1 1 | C |
| 9  | 1 | 1 | 1 | 1 | 1 | 1 1 | 1 1 | 1 1 1 | 5 |
| 10 | 1 | 1 | 1 | 1 | 1 | 1 1 | 1 1 1 | 1 1 1 | 5 |
| 11 | 1 | 1 | 1 | 1 | 1 |   | 1 1 | 1 1 1 | C |
| 12 | 1 | 1 |   |   | 1 | 1 1 | 1 1 1 | 1 1 1 | C |
| 14 | 1 | 1 |   |   | 1 | 1 1 | 1 1 1 | 1 1 | 3 |
| 15 | 1 |   | 1 | 1 | 1 | 1 1 | 1 1 1 | 1 1 1 | 3 |
| 16 | 1 | 1 | 1 | 1 | 1 | 1 1 | 1 1 1 | 1 1 1 | 2 |
| 17 | 1 |   | 1 |   | 1 1 |   | 1 1 1 | 1 | 4 |
| 18 | 1 | 1 | 1 | 1 |   | 1 |   | 1 1 1 | 3 |
| 21 | 1 | 1 | 1 | 1 | 1 | 1 1 |   | 1 1 | 4 |

| Hen No. | 18 Days of Thyroxine Treatment | | | | | | | | | |
|---|---|---|---|---|---|---|---|---|---|---|
|  | 0 | 2 | 4 | 6 | 8 | 10 | 12 | 14 | 16 | 18 |
| 5  | 1 | 1 | 1 |   |   |   | C | M |   |   | E |
| 6  | 1 | 1 |   |   |   |   |   |   | M | E |
| 7  |   |   | 1 |   |   |   | C | M |   |   | E |
| 8  |   |   | 1 | 1 | 1 | 1 1 | 1 | 1 1 | 1 | 1 | E |
| 9  |   | 1 | 1 |   |   |   | C |   | M |   | E |
| 10 | 1 | 1 | 1 | 1 |   | C |   | M |   |   | E |
| 11 | 1 | 1 | 1 | 1 1 | 1 1 | 1 | 1 | 1 | 1 | 1 | E |
| 12 | 1 | 1 | 1 | 1 1 | 1 | 1 1 | 1 1 | 1 | 1 | 1 | E |
| 14 |   | 1 |   | D |   |   |   |   |   |   |  |
| 15 |   | 1 |   |   |   |   | M |   |   |   |  |
| 16 |   | 1 | 1 1 |   |   |   | M C |   |   |   |  |
| 17 | 1 | 1 | 1 |   |   |   |   |   | M |   |  |
| 18 | 1 |   |   |   |   | M | D |   |   |   |  |
| 21 | 1 | 1 |   |   |   |   |   |   | M |   |  |

Notes:
C is control feed;
M is molt feathers;
D is died; and
E is euphanized for necropsy.

Experiment 5. Molting Cobb Broiler Breeder Hens and Roosters with Dietary Thyroxine.

TABLE 12

| 2004 DATE | PEN TRT | 49 CONTROL GROUP | | | 50 Treatment 1 (25 ppm L-thyroxine) | | | 51 Treatment 2 (40 ppm L-thyroxine) | | |
|---|---|---|---|---|---|---|---|---|---|---|
|  |  | # Hens | # Roosters | # Eggs | # Hens | # Roosters | # Eggs | # Hens | # Roosters | # Eggs |
| 13-Sep |  | 30 | 3 | 16 | 30 | 3 | 20 | 30 | 3 | 16 |
| 14-Sep |  | 30 | 3 | 19 | 30 | 3 | 16 | 30 | 3 | 21 |
| 15-Sep |  | 30 | 3 | 17 | 30 | 3 | 11 | 30 | 3 | 15 |
| 16-Sep |  | 30 | 3 | 17 | 30 | 3 | 15 | 30 | 3 | 12 |
| 17-Sep |  | 30 | 3 | 15 | 30 | 3 | 14 | 30 | 3 | 19 |
| 18-Sep |  | 30 | 3 | 20 | 30 | 3 | 11 | 30 | 3 | 19 |
| 19-Sep |  | 30 | 3 | 18 | 30 | 3 | 17 | 30 | 3 | 20 |
| 20-Sep |  | 30 | 3 | 16 | 30 | 3 | 15 | 30 | 3 | 16 |
| 21-Sep |  | 30 | 3 | 17 | 30 | 3 | 14 | 30 | 3 | 16 |
| 22-Sep* |  | 30 | 3 | 18 | 30 | 3 | 14 | 30 | 3 | 18 |
| 23-Sep |  | 30 | 3 | 16 | 30 | 3 | 19 | 30 | 3 | 15 |
| 24-Sep* |  | 30 | 3 | 12 | 30 | 3 | 7 | 30 | 2 | 10 |
| 25-Sep |  | 30 | 3 | 20 | 30 | 3 | 8 | 29 | 2 | 11 |
| 26-Sep |  | 30 | 3 | 18 | 30 | 3 | 9 | 29 | 2 | 6 |
| 27-Sep |  | 30 | 3 | 12 | 30 | 3 | 4 | 29 | 2 | 5 |
| 28-Sep |  | 30 | 3 | 20 | 30 | 3 | 3 | 29 | 1 | 0 |
| 29-Sep |  | 30 | 3 | 19 | 30 | 3 | 1 | 29 | 0 | 1 |
| 30-Sep |  | 30 | 3 | 17 | 30 | 2 | 0 | 29 | 0 | 0 |
| 1-Oct |  | 30 | 3 | 13 | 30 | 2 | 3 | 29 | 0 | 1 |

TABLE 12-continued

| 2004 DATE | PEN TRT | 49 CONTROL GROUP | | | 50 Treatment 1 (25 ppm L-thyroxine) | | | 51 Treatment 2 (40 ppm L-thyroxine) | | |
|---|---|---|---|---|---|---|---|---|---|---|
| | | # Hens | # Roosters | # Eggs | # Hens | # Roosters | # Eggs | # Hens | # Roosters | # Eggs |
| 2-Oct | | 30 | 3 | 17 | 30 | 1 | 1 | 29 | 0 | 0 |
| 3-Oct | | 30 | 3 | 18 | 30 | 1 | 0 | 29 | 0 | 0 |
| 4-Oct | | 30 | 3 | 19 | 30 | 1 | 1 | 28 | 0 | 0 |
| 5-Oct | | 30 | 3 | 16 | 30 | 1 | 1 | 28 | 0 | 0 |
| 6-Oct | | 30 | 3 | 14 | 30 | 1 | 0 | 28 | 0 | 0 |
| 7-Oct | | 30 | 3 | 16 | 30 | 1 | 0 | 28 | 0 | 0 |
| 8-Oct* | | 30 | 3 | 12 | 27 | 0 | 3 | 25 | 0 | 0 |
| 9-Oct | | 30 | 3 | 17 | 27 | 0 | 1 | 25 | 0 | 0 |
| 10-Oct | | 30 | 3 | 12 | 26 | 0 | 0 | 25 | 0 | 0 |
| 11-Oct | | 30 | 3 | 16 | 26 | 0 | 0 | 25 | 0 | 0 |
| 12-Oct | | 30 | 3 | 13 | 26 | 0 | 0 | 25 | 0 | 0 |
| 13-Oct | | 30 | 3 | 17 | 26 | 0 | 0 | 25 | 0 | 0 |
| 14-Oct | | 30 | 3 | 15 | 26 | 0 | 0 | 25 | 0 | 0 |
| 15-Oct | | 30 | 3 | 15 | 25 | 0 | 0 | 25 | 0 | 0 |
| 16-Oct | | 30 | 3 | 12 | 25 | 0 | 0 | 25 | 0 | 0 |
| 17-Oct | | 30 | 3 | 17 | 24 | 0 | 0 | 25 | 0 | 0 |
| 18-Oct | | 30 | 3 | 18 | 24 | 0 | 0 | 25 | 0 | 0 |
| 19-Oct | | 30 | 3 | 9 | 23 | 0 | 0 | 25 | 0 | 0 |
| 20-Oct | | 30 | 3 | 16 | 23 | 0 | 0 | 25 | 0 | 0 |
| 21-Oct | | 30 | 3 | 19 | 23 | 0 | 0 | 25 | 0 | 0 |
| 22-Oct | | 30 | 3 | 10 | 22 | 0 | 0 | 25 | 0 | 0 |
| 23-Oct | | 30 | 3 | 14 | 22 | 0 | 0 | 25 | 0 | 0 |
| 24-Oct | | 30 | 3 | 13 | 21 | 0 | 0 | 25 | 0 | 0 |
| 25-Oct | | 30 | 3 | 20 | 21 | 0 | 0 | 25 | 0 | 0 |
| 26-Oct | | 30 | 3 | 13 | 21 | 0 | 0 | 25 | 0 | 0 |
| 27-Oct | | 30 | 3 | 16 | 21 | 0 | 0 | 25 | 0 | 0 |
| 28-Oct | | 30 | 3 | 12 | 21 | 0 | 0 | 25 | 0 | 0 |
| 29-Oct | | 30 | 3 | 17 | 21 | 0 | 0 | 25 | 0 | 3 |
| 30-Oct | | 30 | 3 | 12 | 21 | 0 | 0 | 25 | 0 | 3 |
| 31-Oct | | 30 | 3 | 13 | 21 | 0 | 0 | 25 | 0 | 3 |
| 1-Nov | | 30 | 3 | 17 | 21 | 0 | 0 | 25 | 0 | 1 |
| 2-Nov | | 30 | 3 | 15 | 21 | 0 | 0 | 25 | 0 | 3 |
| 3-Nov | | 30 | 3 | 13 | 21 | 0 | 0 | 25 | 0 | 3 |
| 4-Nov | | 30 | 3 | 15 | 21 | 0 | 0 | 25 | 0 | 5 |
| 5-Nov | | 30 | 3 | 13 | 21 | 0 | 0 | 24 | 0 | 5 |
| 6-Nov | | 30 | 3 | 11 | 21 | 0 | 0 | 24 | 0 | 4 |
| 7-Nov | | 30 | 3 | 18 | 21 | 0 | 0 | 24 | 0 | 4 |

*Notes:
September 22 - placed on test feed.
September 24 - accidental death of rooster treatment 2.
October 8 - 3 hens sampled per treatment in treatments 1 and 2.

Cobb broiler breeder hens reduced their feed intake, ceased egg production, and began to molt feathers within about 15-17 days on thyroxine treated feed, a very similar but slightly delayed response compared to caged laying hens. Roosters began to "stroke blood" from the nostrils due to heat production and/or increased blood pressure associated with 25 or 40 mg/kg diet inclusion levels of L-thyroxine; therefore, males were unable to tolerate these levels of L-thyroxine apparently due to different hormonal makeup than the hens.

Experiment 6. Molting of Caged Laying with Dietary L-Thyroxine or Thyroactive Iodinated Casein

TABLE 13

Bovans Caged Laying Hen Thyroxine Molting Trial Started May 25, 2005 (End of First Cycle of Egg Production)

| Dietary Treatment[1] | 25 May 2005 Initial Body Wt, lb | 9 Jun. 2005 (9th d Trt) Body Wt Change, lb | Days to 0% Egg Prod. (by Replicate) | 2 & 4 Jun. 2005 Egg Weight, g | 4 Jun. 2005 Shell + Membrane, mm | 9 Jun. 2005 Ovary + Oviduct, % B Wt |
|---|---|---|---|---|---|---|
| Feed Removal | 3.60 | −0.79$^a$ | 9.0$^b$ | 59.78 | 0.395$^b$ | 2.42 |
| 20 mg T$_4$/kg (L-T) | 3.49 | −0.50$^b$ | 12.0$^a$ | 58.68 | 0.466$^a$ | 4.59 |
| 40 mg T$_4$/kg (L-T) | 3.57 | −0.60$^b$ | 11.0$^a$ | 60.17 | 0.446$^a$ | 3.19 |
| 40 mg T$_4$/kg (TIC) | 3.51 | −0.54$^b$ | 11.0$^a$ | 58.46 | 0.424$^a$ | 4.47 |
| P value | 0.35 | <0.001 | <0.001 | 0.23 | <0.001 | >0.43 |

[1]T$_4$ is thyroxine; L-T is L-thyroxine; and TIC is thyroactive iodinated casein. A 7-day pretest began May 25, followed by treatments, with 10 hours of light daily during pretest and treatments.

In Experiment 6, a conventional feed withdrawal molting procedure was compared with 5 dietary thyroxine treatments. Body weight loss after 9 days was greater, days to 0% egg production (9 days) shorter, ovary plus oviduct weight numerically lighter on day 9 of treatment, but eggs collected on day 4 of treatment had thinner shells, in the feed withdrawal group. Thyroactive iodinated casein (TIC) was as effective as L-thyroxine (11 days to 0% egg production and −0.54 lb weight loss each) when contributing 40 mg $T_4$/kg diet. The 10-hour light days during the 7-day pretest and the molting treatment period was evaluated to hasten the cessation of egg production, but unfortunately it appeared to be counterproductive probably due to reduced treated feed intake on the shorter day length.

Following are results of assays of the thyroactive iodinated casein (1% thyroxine) supplemented to diets in Experiment 6. It was manufactured in a foreign country. Assays were conducted at a commercial lab in the U.S. on Sep. 13, 2004 using enzymatic hydrolysis and HPLC.

At 40 mg $T_4$/kg diet, porcine thyroid powder was most effective. The thyroactive iodinated casein alone (40 mg $T_4$/kg diet) or Sigma L-thyroxine (10, 20, or 40 mg $T_4$/kg diet) were not as effective as porcine thyroid powder at regressing reproductive tracts. No feather molt occurred in any treatment during the 10-day molting treatment period.

Although the present invention has been described in the context of compositions, examples, methods, preferred embodiments, procedures, and processes to illustrate further practice of the invention, it will be readily apparent to those skilled in the art that numerous modifications and variations can be made therein without departing from the spirit or scope of the invention. Also, the appended claims of the present invention may be practiced otherwise than as particularly described. It is intended that the above description be interpreted as illustrative, and not in a limiting sense.

TABLE 1

Assay of thyroactive iodinated casein (~1% thyroxine activity) by HPLC.

|  | (MIT; $T_1$) Monoiodotyrosine (%) | (DIT; $T_2$) Diiodotyrosine (%) | ($T_1$; $T_2$) Mono-&Diiodothyronines (%) | ($T_3$) Triiodothyronine (%) | ($T_4$) Thyroxine (%) | "Iodotyrosines" Combined Total (%) |
|---|---|---|---|---|---|---|
| Lot #1 | 1.39 | 2.76 | 0.21 | 0.37 | 0.95 | 5.68 |
| Lot #2 | 1.49 | 3.11 | 0.30 | 0.42 | 0.97 | 6.29 |
| Lot #3 | 1.22 | 2.46 | 0.20 | 0.35 | 0.92 | 5.15 |
| Lot #4 | 1.20 | 2.64 | 0.17 | 0.37 | 0.78 | 5.16 |
| Average | 1.33 | 2.74 | 0.22 | 0.38 | 0.91 | 5.57 |

The thyroactive iodinated casein, also known as thyroprotein, had a combination of iodine compounds indicating partial iodination of tyrosine during the process. The product had an overall average content of 0.91% thyroxine based on assay of samples from 4 lots.

Experiment 7. Molting of Turkey Breeder Hens with Dietary L-Thyroxine, PorcineThyroid Powder, or Thyroactive Iodinated Casein. Turkey breeder hens were molted with various dietary thyroxine treatments at Diamond K Research, Marshville, N.C. (Jun. 20-Jul. 1, 2005). Table 13 contains the necropsy results at the end of the 10-day molting treatment period.

TABLE 13

Effect of dietary thyroxinic compounds fed for 10 days on turkey breeder hen body weight and weights of ovary, oviduct, and liver (Experiment 7).

| Dietary Treatment | Ending (10 d) Body Wt, lb | Ovary Weight, g | Oviduct Weight, g | Liver Weight, g |
|---|---|---|---|---|
| Feed & Water Restriction | 23.67 | 72.7[b] | 70.0[b] | 171.8[a] |
| Control Feed (ad libitum) | 24.07 | 165.2[a] | 119.6[a] | 182.0[a] |
| 10 mg $T_4$/kg (L-T) | 23.03 | 159.1[a] | 124.1[a] | 143.0[bc] |
| 25 mg $T_4$/kg (L-T) | 25.11 | 160.5[a] | 134.7[a] | 144.6[b] |
| 40 mg $T_4$/kg (L-T) | 22.99 | 129.1[a] | 138.7[a] | 141.9[bc] |
| 40 mg $T_4$/kg (TIC) | 23.24 | 132.5[a] | 133.2[a] | 142.6[bc] |
| 40 mg $T_4$/kg (PTP) | 23.15 | 42.1[b] | 69.6[b] | 123.1[c] |
| P value | 0.277 | <0.001 | <0.001 | <0.001 |

[1]$T_4$ is thyroxine;
L-T is L-thyroxine;
TIC is thyroactive iodinated casein; and
PTP is defatted, desiccated porcine thyroid powder. There was a 3-day pretest acclimation period after transporting the turkey hens to the research site. There were 6 individually penned hens (on litter) per treatment.

Each of the following is claimed:

1. A method of inducing cessation of egg production in a domesticated chicken hen comprising administering to the hen an effective amount of thyroxine and/or thyroactive iodinated casein, wherein the thyroactive iodinated casein comprises at least about 1% thyroxine, wherein the administering comprises presenting the effective amount to the hen in feed or water for ingestion by the hen, wherein the hen is provided access ad libitum to the feed or water and wherein the cessation of egg production takes place within from about 5 to about 12 days after initiation of the administering.

2. The method of claim 1 wherein the effective amount comprises (a) pure L-thyroxine or (b) a salt or complex comprising L-thyroxine or (c) a combination of one or more members of the group consisting of L-thyroxine and salts comprising L-thyroxine and complexes comprising L-thyroxine.

3. The method of claim 2 wherein the salt or complex comprising L-thyroxine comprises L-thyroxine-Na pentahydrate or L-thyroxine hydrochloride.

4. The method of claim 1 wherein the hen is a laying hen for production of table eggs.

5. The method of claim 1 wherein the hen is a breeding hen for production of fertile eggs.

6. The method of claim 1 wherein the administering comprises presenting the composition to the hen in feed and the effective amount is about 40 mg thyroxine per kilogram of feed.

7. The method of claim 1 wherein the presenting comprises the provision of the composition to the hen in water and the effective amount is about 23 mg thyroxine per kilogram of water.

* * * * *